(12) United States Patent
Prijovic et al.

(10) Patent No.: US 9,353,140 B2
(45) Date of Patent: May 31, 2016

(54) BQC-G, A TUMOR-SELECTIVE ANTI-CANCER PRODRUG

(75) Inventors: Zeljko M. Prijovic, Taipei (TW); Yu-Lin Leu, Tainan (TW); Steve R. Roffler, Taipei (TW)

(73) Assignee: Academia Sinica, Taipei (TW)

( * ) Notice: Subject to any disclaimer, the term of this patent is extended or adjusted under 35 U.S.C. 154(b) by 740 days.

(21) Appl. No.: 13/512,255

(22) PCT Filed: Nov. 24, 2010

(86) PCT No.: PCT/US2010/058045
§ 371 (c)(1),
(2), (4) Date: Sep. 25, 2012

(87) PCT Pub. No.: WO2011/066418
PCT Pub. Date: Jun. 3, 2011

(65) Prior Publication Data
US 2013/0012467 A1    Jan. 10, 2013

Related U.S. Application Data

(60) Provisional application No. 61/264,294, filed on Nov. 25, 2009.

(51) Int. Cl.
*A61K 31/706* (2006.01)
*C07H 15/26* (2006.01)
*A61P 35/00* (2006.01)
*C07H 15/203* (2006.01)

(52) U.S. Cl.
CPC .................................. *C07H 15/203* (2013.01)

(58) Field of Classification Search
CPC .................................................... C07H 15/203
USPC ..................................... 514/25, 23; 536/17.4
See application file for complete search history.

(56) References Cited

PUBLICATIONS

Sugimori, M., et al., "Synthesis and Antitumor Activity of Ring A- and F-Modified Hexacyclic Camptothecin Analogues", J. Med. Chem., vol. 41, (1998), pp. 2308-2318.
Bosslet, K., et al., "Elucidation of hte Mechanism Enabling Tumor Selective Prodrug Monotherapy[1]", Cancer Research, vol. 58, (1998), pp. 1195-1201.
Burke, T.G., et al., "The Structural Basis of Camptothecin Interactions with Human Serum Albumin: Impact on Drug Stability", J. Med. Chem., vol. 37, (1994), pp. 40-46.
Chen, B.M., et al., Cure of Malignant Ascites and Generation of Protective Immunity by Monoclonal Antibody-Targeted Activation of a Glucuronide Prodrug in Rats, Int. J. Cancer, vol. 73, (1997), pp. 392-402.
De Palma, M., et al., "Immune Cells and Inflammatory Mediators as Regulators of Tumor Angiogenesis", pp. 225-237.
Houba, P.H.J., et al., "Distribution and Pharmacokinetics of the Prodrug Daunorubicin-GA3 in Nude Mice Bearing Human Ovarian Cancer Xenografts", Biochemical Pharmacology, vol. 57, (1999), pp. 673-680.
Houba, P.H.J., et al., "A Novel Doxorubicin-Glucuronide Prodrug DOX-GA3 for Tumour-Selective Chemotherapy: Distribution and Efficacy in Experimental Human Ovarian Cancer", British Journal of Cancer, vol. 84, No. 4, (2001), pp. 550-557.
Juan, T., et al., Antiangiogenesis Targeting Tumor Microenvironment Synergizes Glucuronide Prodrug Antitumor Activity, Clin. Cancer Res., vol. 15, No. 14, (2009), pp. 4600-4611.
Leu, Y., et al., "Design and Synthesis of Water-Soluble Glucuronide Derivatives of Camptothecin for Cancer Prodrug Monotherapy and Antibody-Directed Enzyme Prodrug Therapy (ADEPT)", J. Med. Chem., vol. 42, (1999), pp. 3623-3628.
Leu, Y., et al., "Benzyl Ether-Linked Glucuronide Derivative of 10-Hydroxycamptothecin Designed for Selective Camptothecin-Based Anticancer Therapy", J. Med. Chem., vol. 51, (2008), pp. 1740-1746.
Lu, A., et al., 3D-QSAR Study of 20 (S)-Camptothecin Analogs', Acta Pharmacol. Sin., vol. 28, No. 2, (2007), pp. 307-314.
Mi, Z., et al., "Marked Interspecies Variations Concerning the Interactions of Camptothecin with Serum Albumins: A Frequency-Domain Fluorescence Spectroscopic Study", Biochemistry, vol. 33, (1994), pp. 12540-12545.
Mi, Z., et al., "Reduced Albumin Binding Promotes the Stability and Activity of Topotecan in Human Blood", Biochemistry, vol. 34, (1995), pp. 13722-13728.
Muerdter, T.E., et al., "Dose Optimization of a Doxorubicin Prodrug (HMR 1826) in Isolated Perfused Human Lungs: Low Tumor pH Promotes Prodrug Activation by β-Glucuronidase", The Journal of Pharmacology and Experimental Therapeutics, vol. 301, No. 1, (2002), pp. 223-228.
Prijovic, Z.M., et al., "Anti-Tumor Activity and Toxicity of the New Prodrug 9-Aminocamptothecin Glucuronide (9ACG) in Mice", British Journal of Cancer, vol. 86, (2002), pp. 1634-1638.
Prijovich, Z.M., et al., "Stability of the New Prodrug 9-Aminocamptothecic Glucuronide (9ACG) in the Presence of Human Serum Albumin", Biochemical Pharmacology, vol. 66, (2003), pp. 1181-1187.
Prijovich, Z.M., et al., "Effect of pH and Human Serum Albumin on the Cytotoxicity of a Glucuronide Prodrug of 9-Aminocamptothecin", Cancer Chemother. Pharamcol., (2006).
Rofstad, E.K., et al., "Acidic Extracellular pH Promotes Experimental Metastasis of Human Melanoma Cells in Athymic Nude Mice", Cancer Res., vol. 66, No. 13, (2006), pp. 6699-6707.
Sugimori, M., et al., "Synthesis and Antitumor Activity of Novel Hexacyclic Camptothecin Analogues", J. Med. Chem., vol. 37, (1994), pp. 3033-3039.

*Primary Examiner* — Shaojia Anna Jiang
*Assistant Examiner* — Michael C Henry
(74) *Attorney, Agent, or Firm* — Drinker Biddle & Reath LLP (57) ABSTRACT

The invention relates to the synthesis of a second-generation camptothecin glucuronide prodrug (BQC-G) of a potent anti-cancer camptothecin derivative 5,6-dihydro-4H-benzo[de]quinoline-camptothecin (BQC). BQC-G was over 4000 times more water soluble than BQC, displayed good stability in human plasma and was an excellent substrate for enzymatic hydrolysis by bacterial and human β-glucuronidases. BQC-G was about 30 times less toxic than BQC, but was as toxic as BQC after hydrolysis of the glucuronide moiety by β-glucuronidase. In the presence of human serum albumin, BQC-G displayed lower cytotoxicity ($IC_{50}$=1080 nM) but could be activated by β-glucuronidase to display potent activity ($IC_{50}$=13.3 nM).

10 Claims, 4 Drawing Sheets

BQC-G, A TUMOR-SELECTIVE ANTI-CANCER PRODRUG

BACKGROUND OF THE INVENTION

One of the major obstacles of cancer chemotherapy is lack of tumor specificity which leads to life-threatening toxicity. Tumor selectivity can be enhanced by creating relatively non-toxic prodrugs that are selectively activated in the tumor microenvironment by enzymes, which liberate the anti-neoplastic agent from the prodrug. Tumor cells secrete factors that promote an inflammatory microenvironment enriched in activated myeloid cells, which play a crucial role in facilitating tumor progression, metastasis and angiogenesis. Tumor-infiltrating macrophages and neutrophils secrete factors such as matrix metalloproteinases that enhance tumor growth and invasiveness. Treatment of solid tumors with prodrugs that are selectively activated by enzymes secreted by macrophages or neutrophils is a promising method to enhance the therapeutic index of treatment.

The above summarized information is described in the prior art as follows:

DeFeo-Jones, D. et al., A peptide-doxorubicin 'prodrug' activated by prostate-specific antigen selectively kills prostate tumor cells positive for prostate-specific antigen in vivo. *Nat Med* 2000, 6, 1248-52;

Prijovich, Z. M. et al., Anti-tumour activity and toxicity of the new prodrug 9-aminocamptothecin glucuronide (9ACG) in mice. *Br J Cancer* 2002, 86, 1634-1638;

Wu, W. et al., Targeting Cell-Impermeable Prodrug Activation to Tumor Microenvironment Eradicates Multiple Drug-Resistant Neoplasms. *Cancer Res* 2006, 66, 970-980;

Mantovani, A. et al., Tumor-associated macrophages and the related myeloid-derived suppressor cells as a paradigm of the diversity of macrophage activation. *Human Immunology* 2009, 70, 325-330;

Kim, S. et al., Carcinoma-produced factors activate myeloid cells through TLR2 to stimulate metastasis. *Nature* 2009, 457, 102;

Pollard, J. W. Tumour-educated macrophages promote tumour progression and metastasis. *Nature reviews, Cancer* 2004, 4, 71;

Condeel is, J. et al., Macrophages: Obligate Partners for Tumor Cell Migration, Invasion, and Metastasis. *Cell* 2006, 124, 263-266;

Hagemann, T. et al., Enhanced invasiveness of breast cancer cell lines upon co-cultivation with macrophages is due to TNF-{alpha} dependent up-regulation of matrix metalloproteases. *Carcinogenesis* 2004, 25, 1543-1549;

Nozawa, H. et al., Infiltrating neutrophils mediate the initial angiogenic switch in a mouse model of multistage carcinogenesis. *Proceedings of the National Academy of Sciences of the United States of America* 2006, 103, 12493.

SUMMARY OF THE INVENTION

The present invention includes in one aspect thereof new compounds and compositions of matter useful as agents in cancer therapy and in another aspect, methods of making such novel compounds and compositions of matter.

According to one aspect the invention comprises a novel compound according to formula (I) immediately below:

wherein R is a glucuronide linked via an immolative spacer, or a pharmaceutically acceptable salt thereof. Pharmaceutically acceptable salts are well known and identified in the art and include alkali metal salts such as sodium and potassium and certain alkaline earth metals including Calcium, for example.

According to the present invention a preferred compound is one according to formula (I), set forth above, wherein R is:

Another preferred compound of the present invention is one according to formula (I), above, wherein the glucuronide moiety is hydrolyzed by β-glucuronidases. Another preferred compound according to formula (I), above, in one wherein the solubility of the compound in water based buffers is at least about 775 micrograms per milliliter. Other preferred compounds include those according to formula (I) wherein the compound is stable in human serum and those wherein the compound is cytotoxic to human cancer cells.

According to another aspect, the present invention comprises a pharmaceutical composition containing a therapeutically effective amount of a compound according to formula (I) and a pharmaceutically acceptable carrier that is well known in the art. Yet another aspect comprises treating a cancer patient with an effective amount of a pharmaceutical composition containing a therapeutically effective amount of a compound according to formula (I) and a pharmaceutically acceptable carrier that is well known in the art.

Yet another aspect includes a method for synthesizing the compound of formula (I), above according to the following procedure comprising:

A method for synthesizing the compound of formula I comprising:

(a) contacting D(+)-glucurono-3,6-lactone and sodium methoxide to give methyl 1,2,3,4-tetra-O-acetyl-β-D-glycopyranuronate;

(b) reacting methyl 1,2,3,4-tetra-O-acetyl-β-D-glycopyranuronate and TiBr$_4$ in CH$_2$Cl$_2$ to give methyl 1-bromo-1-deoxy-2,3,4-tri-O-acetyl-α-D-glycopyranuronate;

(c) contacting methyl 1-bromo-1-deoxy-2,3,4-tri-O-acetyl-α-D-glycopyranuronate, 4-hydroxy-3-nitrobenaldehyde, and Ag$_2$O to give methyl 1-O-(2-nitro-4-formylphenyl)-2,3,4-tri-O-acetyl-β-D-glycopyranuronate;

(d) contacting methyl 1-O-(2-nitro-4-formylphenyl)-2,3,4-tri-O-acetyl-β-D-glycopyranuronate, NaBH$_4$ and silica gel in i-PrOH/CHCl$_3$ to give methyl 1-O-[2-nitro-4-(hydroxymethyl)phenyl]-2,3,4-tri-O-acetyl-β-D-glycopyranuronate;

(e) reacting methyl 1-O-[2-nitro-4-(hydroxymethyl)phenyl]-2,3,4-tri-O-acetyl-β-D-glycopyranuronate with methanesulfonyl chloride and triethylamine to give methyl 1-O-[4-(methanesulfonyloxymethyl)-2-nitrophenyl]-2,3,4-tri-O-acetyl-β-D-glycopyranuronate;

(f) reacting methyl 1-O-[4-(methanesulfonyloxymethyl)-2-nitrophenyl]-2,3,4-tri-O-acetyl-β-D-glycopyranuronate with BQC and Cs₂CO₂ to give 10-[4-O-(methyl-2,3,4-tri-O-acetyl-β-D-glycopyranuronate)-3-nitrobenzyloxy]5,6-dihydro-4H-benzo[de]quinoline-camptothecin;

(g) reacting 10-[4-O-(methyl-2,3,4-tri-O-acetyl-β-D-glycopyranuronate)-3-nitrobenzyloxy]5,6-dihydro-4H-benzo[de]quinoline-camptothecin with sodium hydroxide to produce 10-[4-O-(methyl-β-D-glycopyranuronate)-3-nitrobenzyloxy]5,6-dihydro-4H-benzo[de]quinoline-camptothecin; and (h) purifying 10-[4-O-(methyl-β-D-glycopyranuronate)-3-nitrobenzyloxy]5,6-dihydro-4H-benzo[de]quinoline-camptothecin to give 10-[4-O-(β-D-glucopyranuronate)-3-nitrobenzyloxy]camptothecin.

Preferably, the method of synthesis is carried out according to the following procedure:

(a) mixing D(+)-glucurono-3,6-lactone and sodium methoxide in methanol to give methyl 1,2,3,4-tetra-O-acetyl-β-D-glycopyranuronate;

(b) reacting a solution of methyl 1,2,3,4-tetra-O-acetyl-β-D-glycopyranuronate and TiBr₄ in CH₂Cl₂ to give methyl 1-bromo-1-deoxy-2,3,4-tri-O-acetyl-α-D-glycopyranuronate;

(c) mixing a suspension of methyl 1-bromo-1-deoxy-2,3,4-tri-O-acetyl-α-D-glycopyranuronate, 4-hydroxy-3-nitrobenaldehyde, and Ag₂O to give methyl 1-O-(2-nitro-4-formylphenyl)-2,3,4-tri-O-acetyl-β-D-glycopyranuronate;

(d) mixing methyl 1-O-(2-nitro-4-formylphenyl)-2,3,4-tri-O-acetyl-β-D-glycopyranuronate, NaBH₄ and silica gel in i-PrOH/CHCl₃ to give methyl 1-O-[2-nitro-4-(hydroxymethyl)phenyl]-2,3,4-tri-O-acetyl-β-D-glycopyranuronate;

(e) reacting a solution of methyl 1-O-[2-nitro-4-(hydroxymethyl)phenyl]-2,3,4-tri-O-acetyl-β-D-glycopyranuonate in CH₂Cl₂ with methanesulfonyl chloride and triethylamine to give methyl 1-O-[4-(methanesulfonyloxymethyl)-2-nitrophenyl]-2,3,4-tri-O-acetyl-β-D-glycopyranuronate;

(f) reacting methyl 1-O-[4-(methanesulfonyloxymethyl)-2-nitrophenyl]-2,3,4-tri-O-acetyl-β-D-glycopyranuronate with a suspension of BQC and Cs₂CO₂ in anhydrous DMF and purified on silica gel to give 10-[4-O-(methyl-2,3,4-tri-O-acetyl-β-D-glycopyranuronate)-3-nitrobenzyloxy]5,6-dihydro-4H-benzo[de]quinoline-camptothecin;

(g) reacting a suspension of 10-[4-O-(methyl-2,3,4-tri-O-acetyl-β-D-glycopyranuronate)-3-nitrobenzyloxy]5,6-dihydro-4H-benzo[de]quinoline-camptothecin with sodium hydroxide in anhydrous MeOH to produce 10-[4-O-(methyl-β-D-glycopyranuronate)-3-nitrobenzyloxy]5,6-dihydro-4H-benzo[de]quinoline-camptothecin; and (h) purifying 10-[4-O-(methyl-β-D-glycopyranuronate)-3-nitrobenzyloxy]5,6-dihydro-4H-benzo[de]quinoline-camptothecin to recover 10-[4-O-(β-D-glucopyranuronate)-3-nitrobenzyloxy]camptothecin.

BRIEF DESCRIPTION OF THE DRAWINGS

Certain embodiments of the present invention are illustrated in the figures and diagrams set forth herein.

FIG. 2 illustrates the stability and hydrolysis of BQC-G in diagram A. The concentrations of BQC-G (circles) and BQC (squares) in PBS (closed symbols) or human plasma (open symbols) were monitored at 37° C. over 24 hours. Disappearance of 5 μM BQC-G (O) and appearance of BQC (u) was monitored during incubation with 20 ng/ml E. coli β-glucuronidase as shown in diagram B and 2 μg/ml human β-glucuronidase as shown in diagram C. Mean and standard deviations of triplicate determinations are depicted.

DETAILED DESCRIPTION OF THE INVENTION

The present invention was conceived through a series of different observations and interpretations made over a period of time and from a variety of sources as set forth below.

β-glucuronidase is a lysosomal enzyme that accumulates in the tumor microenvironment due to release from tumor cells and tumor-infiltrating macrophages and neutrophils. See Sperker, B. et al., Expression and function of beta-glucuronidase in pancreatic cancer: potential role in drug targeting. *Naunyn Schmiedebergs Arch Pharmacol* 2000, 362, 110-5; Bosslet, K. et al., Elucidation of the mechanism enabling tumor selective prodrug monotherapy. *Cancer Res* 1998, 58, 1195-201; De Palma, M. et al., Immune Cells and Inflammatory Mediators as Regulators of Tumor Angiogenesis; Houba, P. H. J. et al., Distribution and pharmacokinetics of the prodrug daunorubicin-GA3 in nude mice bearing human ovarian cancer xenografts. *Biochem Pharmacol* 1999, 57, 673-680. β-glucuronidase activity in the tumor interstitial space is also enhanced in the low pH microenvironment of solid tumors. See Rofstad, E. K. et al., Acidic Extracellular pH Promotes Experimental Metastasis of Human Melanoma Cells in Athymic Nude Mice. *Cancer Res* 2006, 66, 6699-6707; Sung, S.-Y. et al., Tumor Microenvironment Promotes Cancer Progression, Metastasis, and Therapeutic Resistance. *Current Problems in Cancer* 2007, 31, 36-100. We observed that antiangiogenic therapy greatly potentiated the antitumor activity of a glucuronide prodrug and prolonged the survival of mice bearing resistant human colon cancer xenografts by providing strong β-glucuronidase activity and prodrug delivery through enhanced inflammatory cell infiltration and normalization of tumor vessels in the tumor microenvironment. See Juan, T. Y. et al., Antiangiogenesis targeting tumor microenvironment synergizes glucuronide prodrug antitumor activity. *Clin. CanceRes.* 2009, 15: 4600-4611. We therefore identified β-glucuronidase as an ideal target for the design of non-toxic prodrugs to take advantage of the intratumoral accumulation of macrophages and neutrophils as well as the acidic pH microenvironment in tumors.

Figure 1:
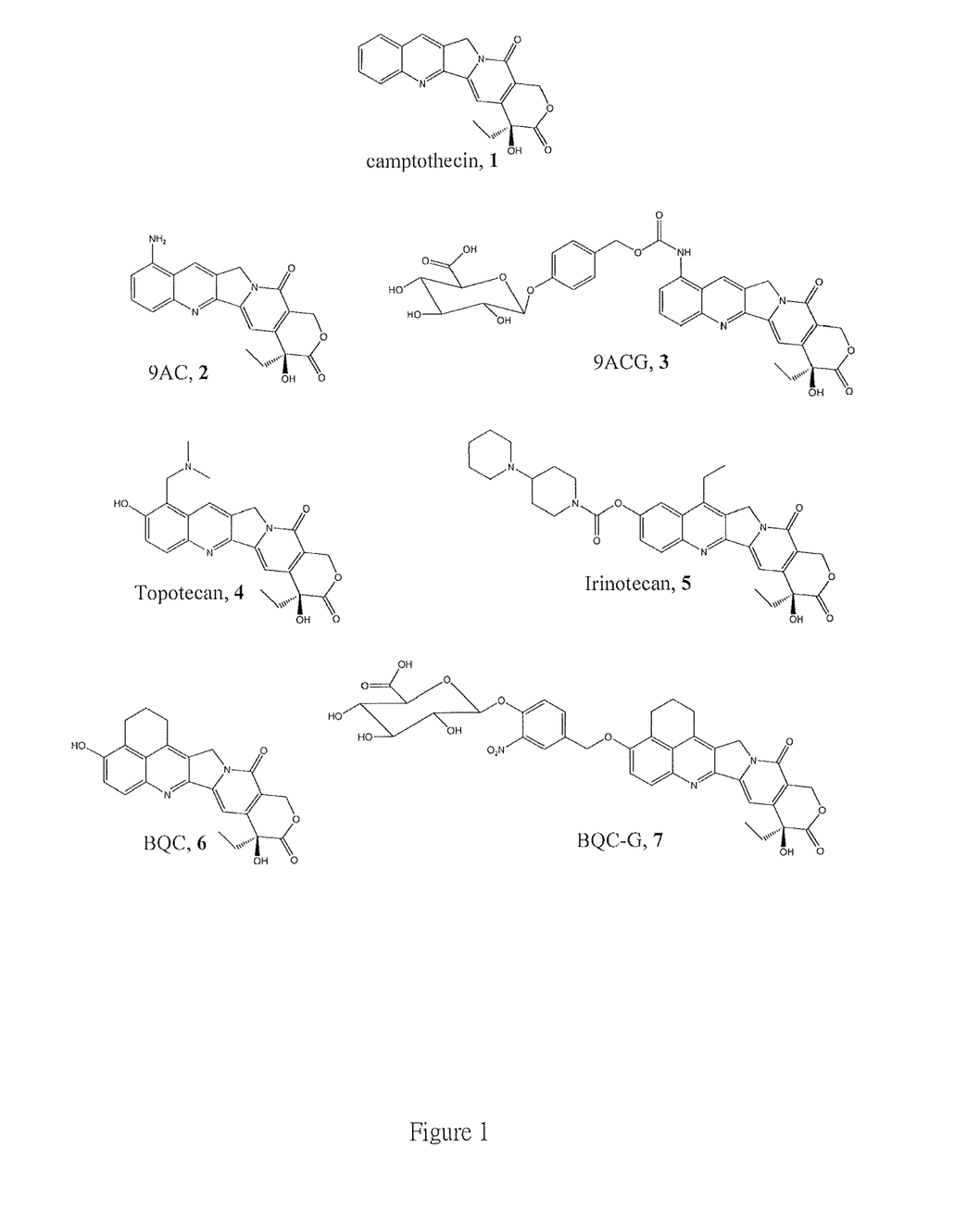
FIG. 1 illustrates the structure of CPT derivatives.

Referring to FIG. 1, we previously described the synthesis of a glucuronide conjugate of the camptothecin (camptothecin, 1) derivative 9-amino-camptothecin (9AC, 2) named 9-amino-camptothecin-glucuronide (9ACG, 3), a DNA topoisomerase I poison which potently stabilizes the covalent attachment of topoisomerase I to single-strand DNA breaks, leading to S-phase specific cell death. See Leu, Y, L. et al., Design and synthesis of water-soluble glucuronide derivatives of camptothecin for cancer prodrug monotherapy and antibody-directed enzyme prodrug therapy (ADEPT). *Journal of Medicinal Chemistry 1999, 42, 3623-8; Hsiang, Y. H. et al., Camptothecin induces protein-linked DNA breaks via mammalian DNA topoisomerase I. *J Biol Chem* 1985, 260, 14873-14878. The 9ACG displayed enhanced solubility and remarkable potency against solid tumors xenografts in mice, further substantiating the utility of β-glucuronidase as a target for prodrug design. See Prijovich et al., *Br J Cancer* 2002, 86, 1634-1638; Leu et al., *Journal of Medicinal Chemistry* 1999, 42, 3623-8. However, in common with CPT, the presence of human serum albumin (HSA) greatly reduced the anticancer activity of 9ACG due to strong binding of 9AC to HSA. See Burke, T. G. et al., The structural basis of camptothecin interactions with human serum albumin: impact on drug stability. *Journal of Medicinal Chemistry* 1994, 37, 40-6; Mi, Z. et al., Marked interspecies variations concerning the interactions of camptothecin with serum albumins: a frequency-domain fluorescence spectroscopic study. *Biochemistry* 1994, 33, 12540-5; Prijovich, Z. M. et al., Stability of the new prodrug 9-aminocamptothecin glucuronide (9ACG) in the presence of human serum albumin. *Biochem Pharmacol* 2003, 66, 1181-1187; Prijovich, Z. M. et al., Effect of pH and human serum albumin on the cytotoxicity of a glucuronide prodrug of 9-aminocamptothecin. *Cancer Chemother Pharmacol* 2007, 60, 7-17. By contrast, the two camptothecin analogs currently approved for clinical use, topotecan (4) and CPT-11 (5), bind more weakly to HSA and remain active in the presence of physiological concentrations of HSA. See Mi, Z. et al., Reduced albumin binding promotes the stability and activity of topotecan in human blood. *Biochemistry* 1995, 34, 13722-8. We concluded that development of tumor-selective camptothecin derivatives that are effective in the presence of HSA is therefore desirable.

Toward the goal of developing a CPT-glucuronide derivative that retains the positive attributes of 9ACG without the negative property of strong albumin binding, we selected a novel 6-ring CPT derivative 5,6-dihydro-4H-benzo[de]quinoline-camptothecin (BQC, 6). See Sugimori, M. et al., Synthesis and antitumor activity of ring A- and F-modified hexacyclic camptothecin analogues. *Journal of medicinal chemistry* 1998, 41, 2308-2318. Based on the minimal HSA binding displayed by topotecan (with a functional group at the C7 position of CPT), we conceived that the presence of a ring spanning the C7 to C9 position in BQC would minimize drug binding to HSA, yet preserve anticancer activity. Hereafter we describe in detail the synthesis and characterization of a prodrug BQC-G (7), in which a glucuronide moiety is linked to BQC vice an immolative spacer.

Chemical Synthesis and Purification

BQC was linked to β-glucuronic acid via a self-immolative benzyl ether spacer following established methods. See Leu, Y.-L. et al., Benzyl ether-linked glucuronide derivative of 10-hydroxycamptothecin designed for selective camptothecin-based anticancer therapy. *Journal of Medicinal Chemistry* 2008, 51, 1740-1746. We employed a linker in BQC-G to overcome problems with direct attachment of glucuronides to CPT derivatives as well as for possible enhancement of enzyme hydrolysis by β-glucuronidase. See Leu, Y.-L. et al., *Journal of Medicinal Chemistry* 1999, 42, 3623-8; Leu, Y.-L. et al., *Journal of Medicinal. Chemistry* 2008, 51, 1740-1746. Reaction Scheme I, depicted below, shows that a mixture of 8 and sodium methoxide in methanol were reacted to give 9, which was reacted with TiBr₄ to yield 10. Coupling 10 with 4-hydroxy-3-nitrobenzaldehyde yielded 11, which was reduced by NaBH₄ to yield 12.

Scheme I

Reagents:
i, Sodium methoxide, MeOH, rt, 1 h
ii, HClO₄, acetic anhydride, rt, 24 h, 46%
iii, TiBr₄, CH₂Cl₂, rt, 24 h, 96%
iv, 4-hydroxy-3-nitrobenzaldehyde, Ag₂O, CH₃CN, rt, 24 h, 50-55%
v, NaBH₄, silica gel, i-PrOH, CHCl₃, 0° C., 1 h, 70-90%

As shown in Reaction Scheme II, below, a solution of 12 in CH₂Cl₂ was reacted with methanesulfonyl chloride and triethylamine to give 13.

Scheme II

Reagents:
i, mesyl chloride, CH₂Cl₂, TEA, 0° C., 1 h

Referring to Reaction Scheme III, below, compound 13 was reacted with a suspension of BQC and $Cs_2CO_3$ in anhydrous DMF and purified on silica gel to give 14. A suspension of 14 was reacted with sodium hydroxide in MeOH to afford the sodium salt of compound 15, then extracted with water. Acidification of the aqueous layer with 1 N HCl and purification by reverse phase column chromatography on silica gel yielded 7 (BQC-G). Highly purified BQC-G (99.90%) was obtained by preparative HPLC on a reverse phase C18 column.

Reagents:
i, BQC(6), $CsCO_3$, DMF, rt, 2 h
ii, $CH_3ONa$, MeOH, 1N HCl

Biological and Efficacy Data

BQC was poorly soluble in water-based buffers (125 ng/ml at pH 4.5 and 200 ng/ml at pH=7.0 (see Table 1). The octanol/water partition coefficient was 1.67 and 1.46 at pH 4.5 and 7.0, respectively. The greater solubility of BQC at pH 7.0 is probably due to spontaneous, pH-mediated opening of the lactone ring to the carboxy form. BQC-G, by contrast, was about 4000 fold more soluble in water based buffers (775 μg/ml at pH=7.0) with an octanol/water partition coefficient of −0.44 and −1.01 at pH 4.5 and 7.0, respectively.

TABLE 1

Solubility and partition coefficient of BQC and BQC-G. Mean values and standard deviations of three independent measurements are shown.

| | BQC | | | BQC-G | | |
|---|---|---|---|---|---|---|
| | water | Buffer pH 4.5 | Buffer pH 7.4 | water | Buffer pH 4.5 | Buffer pH 7.4 |
| Solubility (μg/ml) | 0.200 | 0.120 | 0.200 | ND | ND | 775 |
| Po/w | 1.98 | 1.67 | 1.46 | −0.44 | −0.44 | −1.01 |

ND, not determined.

Figure 2:
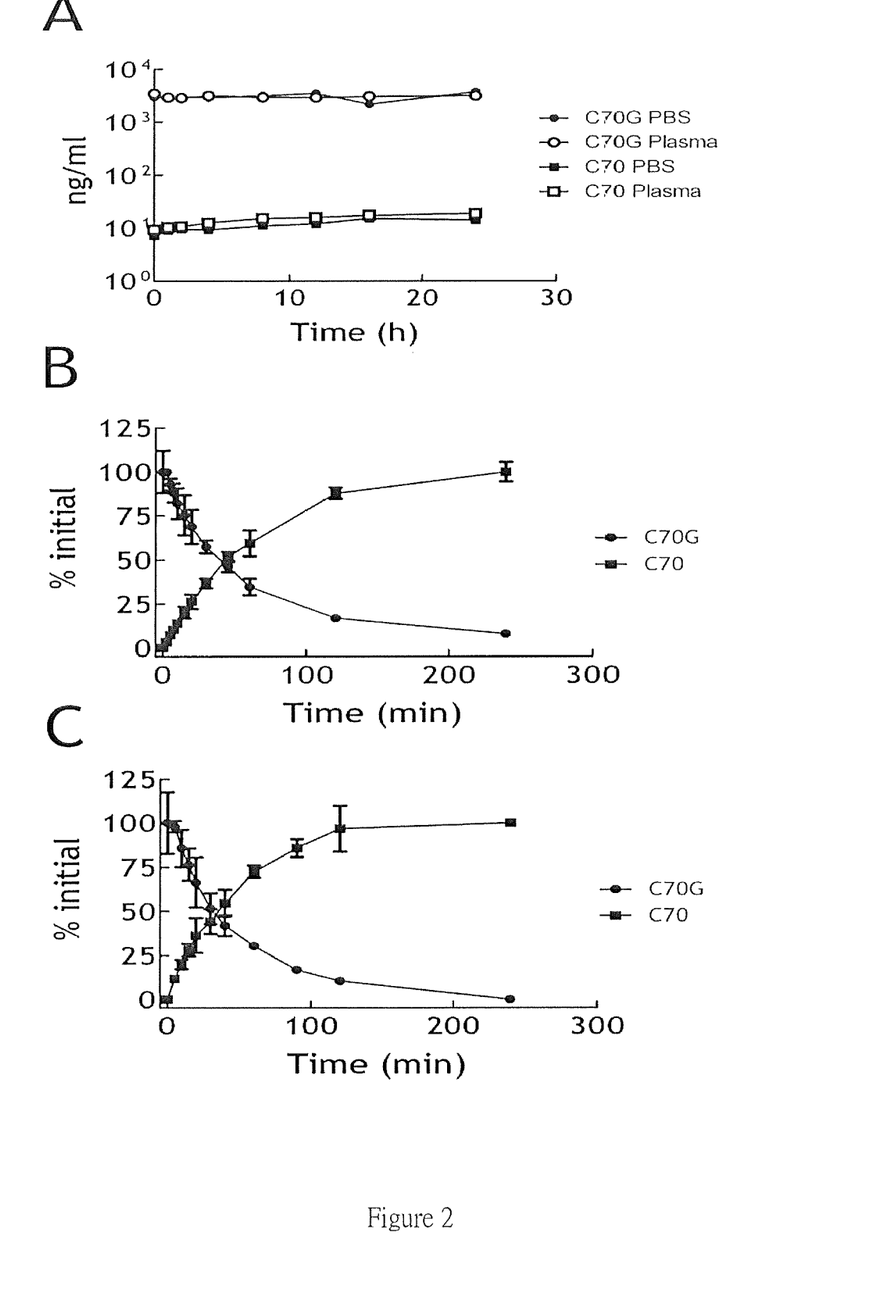

BQC-G was stabile in human serum with only trace amounts of BQC detected after 24 h at 37° C. (see FIG. 2A). On the other hand, BQC-G was an excellent substrate for *E. coli* and human β-glucuronidases and could be completely hydrolyzed by low concentrations of the enzymes to the parental aglycone BQC (see FIG. 2B, C). The kinetic parameters for the β-glucuronidase hydrolysis of BQC-G compare favorably to the widely used β-glucuronidase substrates p-nitrophenol β-D-glucuronide and 4-methylumbelliferyl-β-D-glucuronide (see Table 2).

TABLE 2

Kinetic parameters for the enzymatic hydrolysis of selected glucuronides by *E. coli* β-glucuronidase.

| | Parameter | | |
|---|---|---|---|
| Compound | Km (μM) | Kcat (s$^{-1}$) | Kcat/Km |
| BQC-G | 4.6 ± 0.5 | 45.1 | 9.8 |
| PNPG | 490 ± 84 | 173 | 0.35 |
| 4-MUG | 80.2 ± 12.4 | 22.2 | 0.28 |
| 9ACG | 30.0 | 8.6 | 0.29 |

Figure 3:
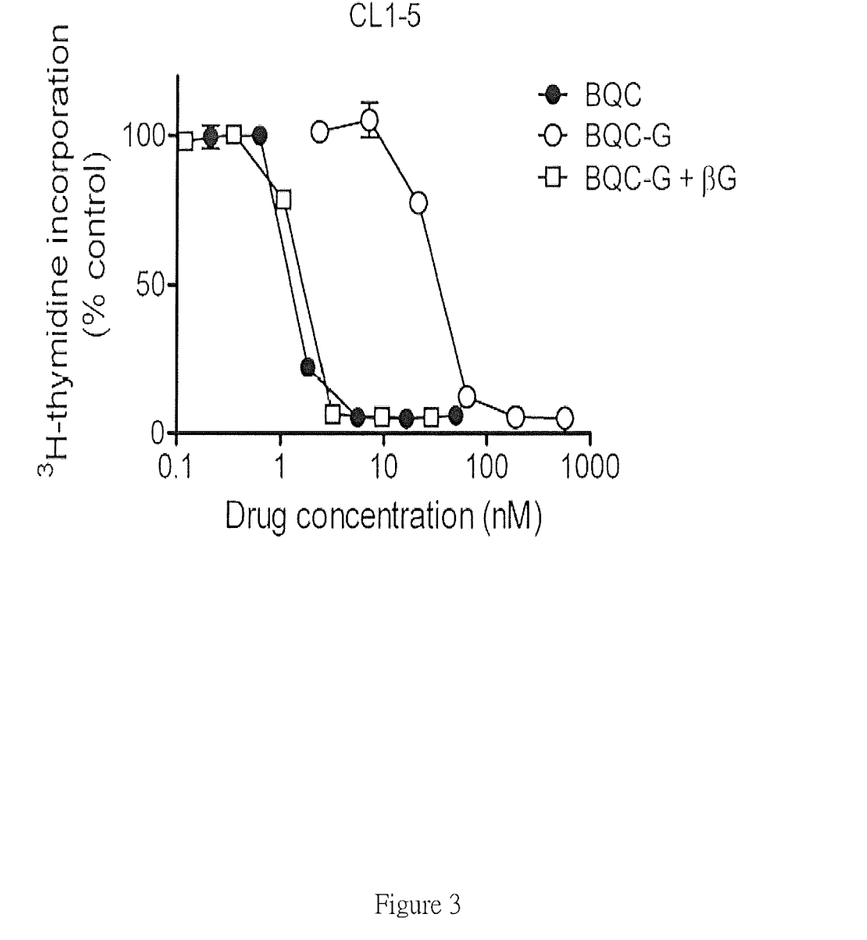
FIG. 3 illustrates inhibitory effect of drugs to CL1-5 human lung adenocarcinoma cells. CL1-5 cells were incubated with the indicated concentrations of BQC, BQC-G or BQC-G plus 1 μg β-glucuronidase. Results show mean levels of $^3$H-thymidine incorporation into the cells (n=3). Bars show the SD.
Figure 4:
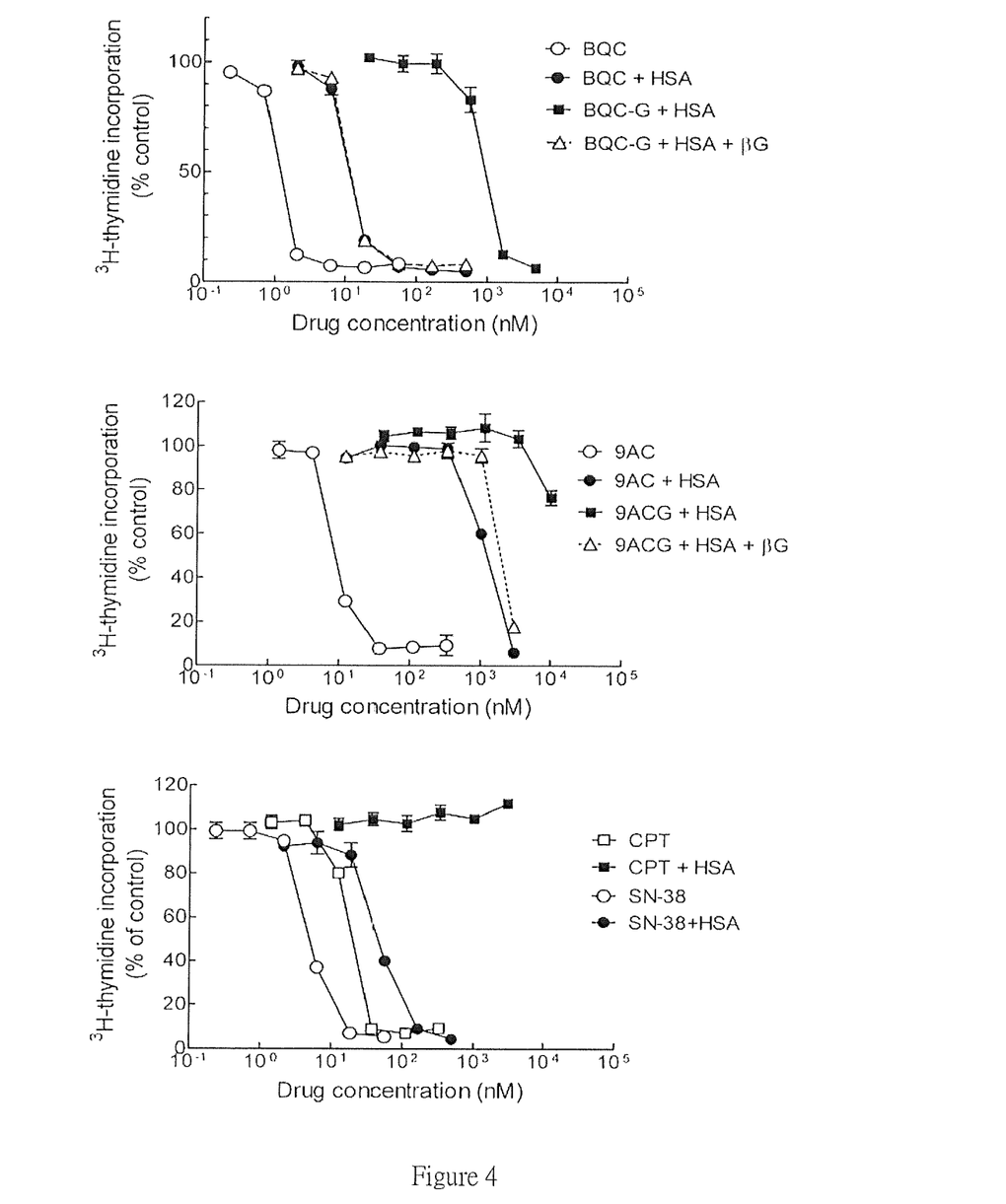
FIG. 4 illustrates cytotoxicity of drugs in the presence of human serum albumin. CL1-5 cells were exposed to the indicated concentrations of drugs with or without the addition of human serum albumin to 40 mg/ml. Results show mean levels of $^3$H-thymidine incorporation into the cells (n=3). Bars show the SD.

BQC displayed potent cytotoxicity to CL1-5 human lung adenocarcinoma cells with an $IC_{50}$ value of 1.4 nM (see FIG. 3). BQC-G was substantially less toxic with an $IC_{50}$ value of 58 nM. Addition of β-glucuronidase with BQC-G resulted in complete restoration of drug cytotoxicity ($IC_{50}$=1.3 nM), consistent with efficient hydrolysis of BQC-G to BQC. Similar $IC_{50}$ values of 1-2 nM were also observed for other cancer cell lines treated with BQC (see Table 3). The effect of HSA on drug cytotoxicity was examined against CL1-5 cells. BQC retained good cytotoxicity ($IC_{50}$=13 nM) in the presence of physiologically relevant levels of HSA (see FIG. 4A). Of note, BQC-G was relatively non-toxic in the presence of HSA ($IC_{50}$=1080 nM) but was effectively hydrolyzed by β-glucuronidase to produce strong cytotoxicity ($IC_{50}$=13 nM) (see FIG. 4A). The effect of HSA on BQC is in stark contrast to 9AC, which displayed a profound decrease in cytotoxicity in the presence of HSA (see FIG. 4B). Similar to 9AC, the cytotoxicity of CPT was drastically reduced in the presence of HSA (see FIG. 4C and Table 4). By contrast, the effect of HSA on BQC cytotoxicity was similar to the effect found for SN-38, the active metabolite of the clinically-used drug CPT-11 (see FIG. 4C).

TABLE 3

Cytotoxicty of drugs to cancer cells. Mean values and SD of triplicate determination are shown.

| | $IC_{50}$ (nM) | | | |
|---|---|---|---|---|
| Cell line | BQC | BQC-G | BQC-G + βG | CPT |
| CL1-5 | 1.37 ± 0.01 | 58.7 ± 2.4 | 1.33 ± 0.03 | 20.5 ± 1.3 |
| LS174T | 1.31 ± 0.03 | 24.6 ± 2.8 | 1.35 ± 0.01 | 9.7 ± 0.8 |
| CaSki | 1.25 ± 0.05 | 31.2 ± 0.5 | 1.44 ± 0.09 | 20 ± 2.1 |
| EJ | 1.78 ± 0.08 | 44.8 ± 0.7 | 2.0 ± 0.1 | 21 ± 3.9 |

TABLE 4

Influence of human serum albumin (HSA) on cytotoxicities of camptothecin drugs toward CL1-5 cells. Mean values and SD of triplicate determinations are shown.

| | $IC_{50}$ (nM) | | |
|---|---|---|---|
| Compound | −HSA | +HSA | Cytotoxicity Ratio[a] |
| BQC | 1.37 ± 0.01 | 13.0 ± 0.3 | 9.5 |
| BQC-G | 58.7 ± 2.4 | 1080 ± 60 | 18.4 |
| BQC-G + βG | 1.33 ± 0.03 | 13.3 ± 0.03 | 10 |
| 9AC | 9.8 ± 0.3 | 1370 ± 70 | 140 |
| 9ACG | 650 ± 40 | >10000 | >15 |
| 9ACG + βG | 26.1 ± 0.4 | 2170 ± 50 | 83 |
| CPT | 20.5 ± 1.3 | >3000 | >146 |
| SN-38 | 5.25 ± 0.08 | 47.9 ± 1.9 | 9.1 |
| topotecan | 27.8 ± 0.3 | 28.4 ± 0.7 | 1.0 |

[a]Ratio of $IC_{50}$ value in the presence of HSA to the $IC_{50}$ value without HSA.

In accordance with the invention, we demonstrated that the glucuronide prodrug BQC-G displays properties consistent with its use in targeted cancer therapy and cancer monotherapy. Our data demonstrated that BQC-G was substantially less toxic than BQC in vitro, but was rapidly converted to BQC by β-glucuronidase. BQC-G displayed even less toxicity in the presence of physiological concentrations of human serum albumin, but remained an excellent substrate for β-glucuronidase. These properties show that BQC-G is a prodrug for the clinical treatment of tumors that display elevated levels of β-glucuronidase due to necrotic release of β-glucuronidase from intracellular stores or to an inflammatory microenvironment.

BQC-G is about 4000 times more water soluble than BQC, facilitating formulation in water-based systems. Moreover, the octanol/water partition coefficient was about −1, indicating that the plasma membrane should be relatively impermeable to BQC-G. The self-immolative spacer between glucuronide acid and BQC appeared to facilitate binding of the prodrug to β-glucuronidase, resulting in a very low Km value of 4.6 μM. Hydrolysis of BQC-G by β-glucuronidase was rapid and complete, confirming that BQC-G is a good substrate for the enzyme and that the spacer was released from BQC.

An important discovery in accordance with our invention was that BQC retained potent cytotoxicity in the presence of physiological concentrations of HSA. The strong binding and deactivation of CPT and 9AC by HSA explains the poor clinical responses observed with these drugs. See Burke, T. G. et al., *Journal of Medicinal Chemistry* 1994, 37, 40-6; Mi, Z. et al., *Biochemistry* 1994, 33, 12540-5; Prijovich, Z. M. et al., Cancer Chemother Pharmacol 2007, 60, 7-17; Mi, Z. et al., Biochemistry 1995, 34, 13722-8. By contrast, BQC retained low nM potency and was more active than the clinically used analogs SN38 (active metabolite of CPT-11) and topotecan even in the presence of 40 mg/ml HSA. Importantly, BQC-G could be completely hydrolyzed to BQC in the presence of HSA and BQC-G cytotoxicity was modulated to a greater degree than BQC, resulting in a greater differential toxicity between prodrug and drug in the presence of HSA. This last point indicates that BQC-G binds HSA more strongly than BQC. We believe that HSA acts as a carrier protein to extend the circulation time of the prodrug and further improve tumor selectivity as has been demonstrated for some HSA-drug conjugates. See Prijovich, Z. M. et al., *Cancer Chemother Pharmacol* 2007, 60, 7-17; Kratz, F., Albumin as a drug carrier: Design of prodrugs, drug conjugates and nanoparticles. *Journal of Controlled Release* 2008, 132, 171-183; Fiehn, C. et al., Targeted drug delivery by in vivo coupling to endogenous albumin: an albumin-binding prodrug of methotrexate (MTX) is better than MTX in the treatment of murine collagen-induced arthritis. *Annals of the rheumatic diseases* 2008, 67, 1188-1191; Wunder, A. et al., Albumin-based drug delivery as novel therapeutic approach for rheumatoid arthritis. *Journal of immunology* (Baltimore, Md.:1950) 2003, 170, 4793-4801; Hariri, G. et al., Radiation-guided Drug Delivery of Nanoparticle Albumin-bound Paclitaxel to Lung Cancer. *International Journal of Radiation Oncology, Biology, Physics* 2008, 72, S705-S706.

β-glucuronidase is an excellent target for selective prodrug activation since this enzyme accumulates in the interstitial tumor space due to release from intracellular stores in necrotic areas. See Bosslet, K. et al., A novel one-step tumor-selective prodrug activation system. *Tumor Targeting* 1995, 1, 45-50; Schumacher, U. et al., Histochemistry of therapeutically relevant enzymes in human tumours transplanted into severe combined immunodeficient (SCID) mice: nitric oxide synthase-associated diaphorase, beta-D-glucuronidase and non-specific alkaline phosphatase. *Acta histochemica* 1996, 98, 381. Moreover, the abundant macrophages and neutrophils present in the inflammatory microenvironment of solid tumors release lysosomal enzymes including β-glucuronidase. See Bosslet, K. et al., *Cancer Res* 1998, 58, 1195-201; Komatsu, N. et al., Heparanase expression in B16 melanoma cells and peripheral blood neutrophils before and after extravasation detected by novel anti-mouse heparanase monoclonal antibodies. *Journal of Immunological Methods* 2008, 331, 82-93. The acidic pH in the tumor microenvironment may further contribute to enhanced β-glucuronidase activity in tumor tissue. See Tannock, I. F. et al., Acid pH in tumors and its potential for therapeutic exploitation. *Cancer Res* 1989, 49, 4373-84; Gerweck, L. E., Tumor pH: Implications for treatment and novel drug design. *Seminars in Radiation Oncology* 1998, 8, 176-182. We and others have shown that monotherapy with glucuronide prodrugs can selectively kill solid tumors and be preferentially activated in human tumor samples, further validating the utility of β-glucuronidase as a target for the design of selective antineoplastic prodrugs. See Prijovich, Z. M. et al., *Br J Cancer* 2002, 86, 1634-1638; Bosslet, K. et al., *Cancer Res* 1998, 58, 1195-201; Houba, P. H. et al., A novel doxorubicin-glucuronie prodrug DOX-GA3 for tumour-selective chemotherapy: distribution and efficacy in experimental human ovarian cancer. *Br J Cancer* 2001, 84, 550-7; Mürdter, T. E. et al., Dose optimization of a doxorubicin prodrug (HMR 1826) in isolated perfused human lungs: low tumor pH promotes prodrug activation by beta-glucuronidase. *J Pharmacol Exp Ther* 2002, 301, 223-228. More recently, we discovered that therapy with an antiangiogenesis antibody strongly enhanced the efficacy of glucuronide prodrug monotherapy by increasing inflammatory cell infiltration in the tumor microenvironment and normalization of tumor vessels. See Juan, T. Y. et al., *Clin. Cancer Res.* 2009, 15: 4600-4611. Taken together, these studies indicate that glucuronide prodrugs such as BQC-G are good candidates to increase the therapeutic index of cancer chemotherapy.

Besides relying on the accumulation of β-glucuronidase by natural mechanisms, several methods to enrich β-glucuronidase activity in tumors are under development including targeting β-glucuronidase as an antibody-enzyme conjugate (ADEPT), expressing β-glucuronidase from viral or non-viral vectors (GDEPT) and selective enrichment of β-glucuronidase expressing bacteria in tumors (BacDEPT). See Houba, P. H. J. et al., *Biochem Pharmacol* 1999, 57, 673-680; Leu, Y. L. et al., *Journal of Medicinal Chemistry* 1999, 42, 3623-8; Prijovich, Z. M. et al., *Biochem Pharmacol* 2003, 66, 1181-1187; Bakina, E. et al., Intensely cytotoxic anthracycline prodrugs: glucuronides. *J Med Chem* 1997, 40, 4013-8; Chen, K. C. et al., Membrane-localized activation of glucuronide prodrugs by beta-glucuronidase enzymes. *Cancer Gene Ther* 2007, 14, 187-200; de Graaf, M. et al., A fully human anti-Ep-CAM scFv-beta-glucuronidase fusion protein for selective chemotherapy with a glucuronide prodrug. *Br J Cancer* 2002, 86, 811-8; de Graaf, M. et al., Pronounced antitumor efficacy by extracellular activation of a doxorubicin-glucuronide prodrug after adenoviral vector-mediated expression of a human antibody-enzyme fusion protein. *Hum Gene Ther* 2004, 15, 229-38; Cheng, C. M. et al., Tumor-targeting prodrug-activating bacteria for cancer therapy. *Cancer Gene Ther* 2008. Although these targeting strategies are more complex, they offer the possibility of extending glucuronide prodrug treatment to smaller tumors without necrotic regions and to those tumors that are not heavily infiltrated with monocytes. Overall, our data demonstrate that BQC-G is a potent prodrug for monotherapy as well as targeted therapy of tumors.

EXAMPLES

Materials 5,6-dihydro-4H-benzo[de]quinoline camptothecin (BQC) was supplied from Daichi, Tokyo, Japan. CPT and CPT-11 were from Sigma-Aldrich (St. Louis, Mo.). SN-38 was from ScinoPharm (Shan-Hua, Taiwan). Topotecan hydrochloride was from SmithKline Beecham Pharmaceuticals (Philadelphia, Pa.). The 9ACG was synthesized as described. See Leu, Y. L., *Journal of Medicinal Chemistry* 1999, 42, 3623-8.

The cancer cell lines were from ATCC except for CL1-5 human lung adenocarcinoma which was generous gift from Dr. PC Yang and EJ human bladder carcinoma cells. See Yang, P. C. et al., Characterization of the mucin differentiation in human lung adenocarcinoma cell lines. *American journal of respiratory cell and molecular biology* 1992, 7, 161-171; Marshall, C. J. et al., Markers of neoplastic transformation in epithelial cell lines derived from human carcinomas. *J Natl Cancer Inst* 1977, 58, 1743-51.

Coarse (40-60 μm particle size) LiChroprep C18 for SPE was from Merck (Darmstadt, Germany) and C-18 analytical column μBondapak 10 μm with Guard-pak precolumn insert were from Waters (Milford, Mass., U.S.A.).

Analytical Methods

Melting points were determined with a Keller apparatus and are uncorrected. Reaction courses were routinely monitored by thin-layer chromatography (TLC) on silica gel precoated Durasil-25 UV254 Merck plates with detection under 254 nm UV lamp or heating. Nuclear magnetic resonance ($^1$H NMR) spectra were determined in DMSO-$d_6$ or CDCl$_3$ solution with a Broker AC-200 spectrometer and chemical shifts are given in pap from internal tetramethylsilane as a standard. Column chromatography was performed with Merck 70-230 mesh silica gel. Reverse column chromatography was performed with LiChroprep RP-18 (40-63 μm) by our method originally developed for CPT-11 and its metabolites. See Prijovich, Z. M. et al., Local enzymatic hydrolysis of an endogenously generated metabolite can enhance CPT-11 anticancer efficacy. *Mol Cancer Ther* 2009, 8, 940-6.

Methyl 1,2,3,4-tetra-O-acetyl-β-D-glucopyranuronate, compound 9, Scheme I

A mixture of D (+)-glucurono-3,6-lactone (8) (88 g, 500 mmol) and CH$_3$ONa (0.75 g, 13.9 mmol) in methanol (500 ml) was stirred at room temperature for 2 h. The reaction mixture was concentrated under reduced pressure to give a yellow-orange oily residue. To the residue was added acetic anhydride (340 ml). A solution of perchloric acid (1.5 ml) in acetic anhydride (10 ml) was then added to the mixture dropwise in an ice bath and stirred for 2 h. The resulting precipitate was recrystallized by methanol to give 9 (86 g, 46%) mp 176° C., $^1$H NMR (200 MHz, DMSO-$d_6$) δ 1.98 (t, J=4.6 Hz, 9H), 2.07 (s, 3H), 3.62 (s, 3H), 4.65 (d, J=9.8 Hz, H), 4.98 (q, J=8.4 Hz, 2H), 5.50 (t, J=9.5 Hz, 1H), 6.00 (d, J=8.1 Hz, 1H); $^{13}$C NMR (50 MHz, DMSO-$d_6$) δ 21.0, 21.1, 21.2, 21.3, 53.5, 69.7, 70.7, 71.7, 72.3, 91.5, 167.8, 169.6, 169.9, 170.2, 170.3.

Methyl 1-bromo-1-deoxy-2,3,4-tri-O-acetyl-α-D-glucopyranuronate, compound 10, scheme I A solution of 9 (1 g, 2.66 mmol) and TiBr$_4$ (1 g, 2.72 mmol) in CH$_2$Cl$_2$ (30 ml) was stirred at room temperature for 24 h. The mixture was washed with ice water (30 ml) and saturated aqueous NaHCO$_3$ solution (30 ml), dried over Na$_2$SO$_4$, and evaporated to dryness to give 10 (0.95 g, 90%), which was used directly in the next step without further purification.

Methyl 1-O-(2-nitro-4-formylphenyl)-2,3,4-tri-O-acetyl-β-D-glucopyranuronate, compound 11, scheme I A suspension of 10 (0.95 g, 2.4 mmol), 4-hydroxy-3-nitrobenzaldehyde (0.44 g, 2.6 mmol) and Ag$_2$O (0.6 g, 2.6 mmol) in CH$_3$CN (50 ml) was stirred at room temperature for 4 h. AgBr was filtered out. The solvent was removed under reduced pressure to give a dark brown crude product, which was washed with methanol to give 11 (0.95 g; 82%). mp 180-182° C., $^1$H NMR (200 MHz, DMSO-$d_6$) δ 2.02 (d, J=3.6 Hz, 9H), 3.64 (s, 3H), 4.81 (d, J=9.6 Hz, 1H), 5.16 (q, J=7.7 Hz, 2H), 5.48 (t, J=9.3 Hz, 1H), 5.95 (d, J=7.5 Hz, 1H), 7.65 (d, J=8.7 Hz, 1H), 8.23 (d, J=6.9 Hz, 1H), 8.45 (d, J=1.7 Hz, 1H), 9.99 (s, 1H); $^{13}$C NMR (50 MHz, DMSO-$d_6$) δ 21.0, 21.1, 21.2, 53.5, 69.3, 70.5, 71.3, 72.1, 98.1, 118.5, 127.1, 131.9, 135.6, 141.1, 152.9, 167.7, 169.6, 170.2, 170.4, 191.4; EI MS m/z 424 (M$^+$—OCOCH$_3$) Anal. (C$_{20}$H$_{21}$O$_{13}$N): Calc. C, 49.55; H, 4.68; N, 2.89. Found. C, 49.46; H, 4.49; N, 2.73.

Methyl 1-O-[2-nitro-4-(hydroxymethyl)phenyl]-2,3,4-tri-O-acetyl-β-D-glucopyranuronate, compound 12, scheme I A mixture of 11 (0.9 g, 1.86 mmol), NaBH$_4$ (0.14 g, 3.72 mmol) and silica gel (2 g) in i-PrOH/CHCl$_3$ (1:5) (60 ml) was stirred at 0° C. for 1 h. The reaction was quenched with 1N HCl and filtered to remove silica gel. The organic layer was washed by water, then dried over anhydrous Na$_2$SO$_4$ and evaporated under reduced pressure to give a residue which was crystallized with EtOH to give 12 (0.8 g, 89%) mp 167-168° C., $^1$H NMR (200 MHz, DMSO-$d_6$) δ 1.98 (d, J=4.0 Hz, 9H) 3.63 (s, 3H), 4.49 (s, 2H), 4.71 (d, J=9.8 Hz, 1H), 5.07 (t, J=9.5 Hz, 2H), 5.44 (t, J=9.4 Hz, 2H), 5.69 (d, J=7.74 Hz, 1H), 7.37 (d, J=8.6 Hz, 1H), 7.59 (d, J=8.6 Hz, 1H), 7.78 (s, 1H); $^{13}$C NMR (50 MHz, DMSO-$d_6$) δ 21.0, 21.1, 21.2, 53.5, 62.2, 69.6, 70.8, 71.7, 71.9, 98.9, 118.6, 123.2, 1319, 139.4, 141.1, 147.8, 167.8, 169.6, 170.2, 170.4; FABMS m/z 426 (M$^+$—OCOCH$_3$).

Methyl 1-O-[4-(methanesulfonyloxymethyl)-2-nitrophenyl]-2,3,4-tri-O-acetyl-β-D-glucopyranuronate, compound 13, of Scheme II A solution of 12 (800 mg, 1.65 mmol) in CH$_2$Cl$_2$ (50 ml) was stirred with methanesulfonyl chloride (0.2 ml, 2.8 mmol) and triethylamine (0.4 ml, 2.97 mmol) at 0° C. for 1 h. The mixture was quenched with saturated aqueous NaHCO$_3$ solution, dried with anhydrous MgSO$_4$, and evaporated to dryness to give 13 (0.88 g, 95%) mp 110-112° C., $^1$H NMR (200 MHz, DMSO-$d_6$) δ 2.00 (s, 9H), 3.27 (s, 3H), 3.63 (s, 3H), 4.74 (d, J=9.8 Hz, 1H), 5.10 (q, J=7.48 Hz, 2H), 5.29 (s, 2H), 5.46 (t, J=9.4 Hz, 1H), 5.77 (d, J=7.7 Hz, 1H), 7.47 (d, J=8.4 Hz, 1H), 7.79 (d, J=8.6 Hz, 1H), 8.02 (s, 1H); FABMS m/z 562 (M$^+$-1).

10-[4-O-(Methyl-2,3,4-tri-O-acetyl-β-D-glucopyranuronate)-3-nitrobenzyloxy]5,6-dihydro-4H-benzo[de]quinoline-camptothecin, compound 14 of scheme III To a suspension of BQC (500 mg, 1.24 mmol) and Cs$_2$CO$_3$ (423 mg, 1.3 mmol) in anhydrous DMF (50 ml) was added compound 13 (0.836 g, 1.5 mmol). The mixture was stirred at room temperature for 2 h. The solvent was removed under vacuum before the solution was added silica gel (5 g). The crude product was purified by column chromatography on silica gel (MeOH/CHCl$_3$=2:98) to give 14 (160 mg, 15%). $^1$H NMR (200 MHz, DMSO-$d_6$) δ 0.87 (t, J=7.1 Hz, 3H, CH$_3$) 1.84-1.88 (m, 2H, CH$_2$), 1.88-2.00 (m, 2H, CH$_2$), 2.01-2.03 (m, 9H, CH$_3$), 2.93-2.94 (m, 2H, CH$_2$), 3.05-3.06 (m, 2H, CH$_2$), 3.63 (s, 3H, OCH$_3$), 4.71 (d, J=9.7 Hz, 1H, sugar-H), 5.08-5.18 (m, 2H, sugar-H), 5.25 (s, 2H, CH$_2$), 5.31 (s, 2H, CH$_2$), 5.40-5.52 (m, 1H, sugar-H), 5.74 (d, J=8.0 Hz, 1H, sugar-H), 6.52 (s, 1H, OH), 7.27 (s, 1H, Ar—H), 7.35-7.71 (m, 3H, Ar—H), 7.74-7.95 (m, 1H, Ar—H), 8.10 (s, 2H, Ar—H), 8.53 (s, 1H, Ar—H).

10-[4-O-(Methyl-β-D-glucopyranuronate)-3-nitrobenzyloxy]camptothecin, compound 15 of Scheme III A suspension of 14 (160 mg, 0.18 mmol) and sodium methoxide (10 mg, 0.2 mmol) in anhydrous MeOH (30 ml) was stirred at room temperature for 2 h. The crude product was dissolved in dichloromethane/water (1:1) solution (20 ml). The dichloromethane layer evaporated to dryness to give 15 (20 mg, 15%). $^1$H NMR (200 MHz, DMSO-$d_6$) δ 0.82 (t, J=7.2 Hz, 3H, CH$_3$), 1.75-1.77 (m, 2H, CH$_2$), 1.88-1.91 (m, 2H, CH$_2$), 2.72-2.82 (m, 2H, CH$_2$), 2.95-3.01 (m, 2H, CH$_2$), 3.32-3.48 (m, 3H, sugar-H), 3.64 (s, 3H, OCH$_3$), 4.13 (d, J=8.9 Hz, 1H, sugar-H), 5.26-5.53 (m, 9H), 6.51 (s, 1H), 7.27 (s, 1H), 7.47-7.62 (m, 3H), 7.81 (d, J=8.3 Hz, 1H), 8.08 (d, J=8.6 Hz, 2H), 8.53 (s, 1H).

10-[4-O-(β-D-glucopyranuronate)-3-nitrobenzyloxy] camptothecin, compound (BQCG,7) of Scheme III The aqueous layer was acidified with 1 N HCl and purified by reverse phase column chromatography on silica gel ($CH_3CN/H_2O$=1:5) to give 7 (35 mg, 27%). LCMS m/z 731.6 ($M^+$). The purified product was further purified by HPLC to provide the material suitable for activity experiments where even low level of active contaminant is undesirable. The product is dissolved in DMSO to 10 mg/ml and then diluted 4 times with 10 mM $KH_2PO_4$ pH=2.6 and filtered through 0.45 μm syringe filter and injected into a RP column packed with LichroPrep 40-60 μm. Separation occurred using 30% ACN in 10 mM $KH_2PO_4$ pH=2.9 at 5 ml/min. Peaks were monitored by UV/Vis at 375 nm and by fluorescence at 340-360 nm excitation and 395-545 nm emission. The peak eluting at 180-200 min was collected. The remaining substances on the column were eluted with 50% ACN in water. To desalt, the product was diluted two-fold with water and applied to the column. After washing the column with 10% ACN in water, BQC-G was eluted with 50% ACN in water and evaporated under vacuum to remove ACN. DMSO was then added and evaporated to 1.5 ml. The product was quantified by enzymatic hydrolysis and stored at -80° C.

Identification and Quantification

Pure BQC-G (1 μg/ml) was dissolved in 0.1 M phosphate buffer pH 7.0. One hundred μl solution was incubated with 1 μg of recombinant *E. coli* β-glucuronidase for 30 min at 37° C. and was then analyzed by SPE-HPLC. A single peak disappeared and a new single peak appeared with a retention time corresponding to BQC.

SPE-HPLC

Samples were diluted with an equal volume of a mixture of acetonitrile (ACN):methanol:0.5 M TCA 4:4:2 (v/v) and then vortex mixed. The mixture was centrifuged 5 min at 15,000×g at 4° C. The clear supernatant was diluted in an equal volume of 0.1 M $KH_2PO_4$, pH 2.9 and injected to a SPE column with an automatic injector. The SPE column was washed for 2.5 min with 20% methanol in 25 mM $KH_2PO_4$, pH 2.9 at 1 ml/min. A 6-port valve was employed to switch the follow of mobile phase (30% ACN 0.1 M $KH_2PO_4$, pH 2.9) in the reverse direction at 1.5 ml/min through the SPE column to transfer the analytes to the analytical column where were separated and detected by fluorescence after excitation at 375 nm and emission at 575 nm for BQC and 460 nm for BQC-G. Retention times were 9.0 min for BQC and 12.2 min for BQC-G.

Water Solubility

BQC or BQC-G was added to water, 0.1 M acetate buffer pH 4.5 or phosphate buffer pH 7.0 and equilibrated 24 h at RT with shaking. Mixtures were centrifuged for 40 min at 20,000 g at room temperature. A sample from the water layer was analyzed by HPLC and quantified using standard curves generated with pure BQC and BQC-G.

Octanol/Water Partition Coefficient

Octanol was pre-equilibrated 24 h at RT with water, 0.1 M acetate buffer, pH 4.5 or 0.1 M phosphate buffer, pH 7.0. One μg of either BQC or BQC-G was added to a mixture of 250 μl octanol and 250 μl of one of the three water based pre-equilibrated solvents. After mixing for 24 h at RT, the samples were centrifuged 20 min at 10,000×g. Samples of the octanol and water layers were analyzed by HPLC.

Stability in Blood

Normal human plasma was spiked with BQC-G to 5 μM. The mixture was incubated 24 h at 37° C. during which time samples were periodically removed and analyzed by SPE-HPLC.

Hydrolysis of BQC-G by β-glucuronidase

One hundred ng of recombinant *E. coli* β-glucuronidase or 2 ug/ml human β-glucuronidase were added to 1 ml of BQC-G (5 nM) in 0.1 M phosphate buffer, pH 7.0 and incubated at 37° C. Samples of 100 μl were periodically removed and BQC and BQC-G were quantified by SPE-HPLC.

In Vitro Cytotoxicity

5000-10000 cells/well in 96 well plate were exposed to graded concentration of the compounds for 48 h in the absence or presence of 40 mg/ml HSA. *E. coli* β-glucuronidase (1 μg/well) was added with BCC-G in some experiments. The cells were washed twice with PBS and incubated in fresh medium for 24 h before the cells were pulsed with 1 μC/well of $^3$H-thimidine for 16 h. Cellular radioactivity in harvested cells was counted on a Topcount scintillation counter and $IC_{50}$ values were calculated by fitting the data to a sigmoidal dose/response equation.

Each and every published paper or reference cited above and herein is hereby incorporated by reference.

It will be apparent to those skilled in the art that modifications and variations may be made to the present invention without departing from the spirit or scope of the invention. It is intended that the present invention covers such modifications and variations.

What is claimed is:

1. A compound according to the formula I, below:

wherein R is a glucuronide linked via an immolative spacer, or a pharmaceutically acceptable salt thereof.

2. A compound according to claim 1 wherein R is

3. The compound according to claim 1 wherein the glucuronide moiety is hydrolyzed by β-glucuronidases.

4. The compound according to claim 1 wherein the solubility of the compound in water based buffers is at least approximately 775 micrograms per milliliter.

5. The compound according to claim 1 wherein the compound is stable in human serum.

6. The compound according to claim 3 wherein the compound is cytotoxic to human cancer cells.

7. A pharmaceutical composition comprising a therapeutically effective amount of a compound according to claim 1 and a pharmaceutically acceptable carrier.

8. A method of treating a cancer patient which comprises administering to the cancer patient an effective amount of a pharmaceutical composition containing a therapeutically effective amount of a compound of formula (I) and a pharmaceutically acceptable carrier.

9. A method for synthesizing the compound of formula I comprising:
(a) contacting D(+)-glucurono-3,6-lactone and sodium methoxide to give methyl 1,2,3,4-tetra-O-acetyl-β-D-glycopyranuronate;
(b) reacting methyl 1,2,3,4-tetra-O-acetyl-β-D-glycopyranuronate and TiBr$_4$ in CH$_2$Cl$_2$ to give methyl 1-bromo-1-deoxy-2,3,4-tri-O-acetyl-α-D-glycopyranuronate;
(c) contacting methyl 1-bromo-1-deoxy-2,3,4-tri-O-acetyl-α-D-glycopyranuronate, 4-hydroxy-3-nitrobenaldehyde, and Ag$_2$O to give methyl 1-O-(2-nitro-4-formylphenyl)-2,3,4-tri-O-acetyl-β-D-glycopyranuronate;
(d) contacting methyl 1-O-(2-nitro-4-formylphenyl)-2,3,4-tri-O-acetyl-β-D-glycopyranuronate, NaBH$_4$ and silica gel in i-PrOH/CHCl$_3$ to give methyl 1-O-[2-nitro-4-(hydroxymethyl)phenyl]-2,3,4-tri-O-acetyl-β-D-glycopyranuronate;
(e) reacting methyl 1-O-[2-nitro-4-(hydroxymethyl)phenyl]-2,3,4-tri-O-acetyl-β-D-glycopyranuronate with methanesulfonyl chloride and triethylamine to give methyl 1-O-[4-(methanesulfonyloxymethyl)-2-nitrophenyl]-2,3,4-tri-O-acetyl-β-D-glycopyranuronate;
(f) reacting methyl 1-O-[4-(methanesulfonyloxymethyl)-2-nitrophenyl]-2,3,4-tri-O-acetyl-β-D-glycopyranuronate with BQC and Cs$_2$CO$_2$ to give 10-[4-O-(methyl-2,3,4-tri-O-acetyl-β-D-glycopyranuronate)-3-nitrobenzyloxy]5,6-dihydro-4H-benzo[de]quinoline-camptothecin;
(g) reacting 10-[4-O-(methyl-2,3,4-tri-O-acetyl-β-D-glycopyranuronate)-3-nitrobenzyloxyl]5,6-dihydro-4H-benzo[de]quinoline-camptothecin with sodium hydroxide to produce 10-[4-O-(methyl-β-D-glycopyranuronate)-3-nitrobenzyloxy]5,6-dihydro-4H-benzo[de]quinoline-camptothecin; and
(h) purifying 10-[4-O-(methyl-β-D-glycopyranuronate)-3-nitrobenzyloxy]5,6-dihydro-4H-benzo[de]quinoline-camptothecin to give 10-[4-O-β-D-glucopyranuronate)-3-nitrobenzyloxy]camptothecin.

10. A method for synthesizing the compound of formula I comprising:
(a) mixing D(+)-glucurono-3,6-lactone and sodium methoxide in methanol to give methyl 1,2,3,4-tetra-O-acetyl-β-D-glycopyranuronate;
(b) reacting a solution of methyl 1,2,3,4-tetra-O-acetyl-β-D-glycopyranuronate and TiBr$_4$ in CH$_2$Cl$_2$ to give methyl 1-bromo-1-deoxy-2,3,4-tri-O-acetyl-α-D-glycopyranuronate;
(c) mixing a suspension of methyl 1-bromo-1-deoxy-2,3,4-tri-O-acetyl-α-D-glycopyranuronate, 4-hydroxy-3-nitrobenaldehyde, and Ag$_2$O to give methyl 1-O-(2-nitro-4-formylphenyl)-2,3,4-tri-O-acetyl-β-D-glycopyranuronate;
(d) mixing methyl 1-O-(2-nitro-4-formylphenyl)-2,3,4-tri-O-acetyl-β-D-glycopyranuronate, NaBH$_4$ and silica gel in i-PrOH/CHCl$_3$ to give methyl 1-O-[2-nitro-4-(hydroxymethyl)phenyl]-2,3,4-tri-O-acetyl-β-D-glycopyranuronate;
(e) reacting a solution of methyl 1-O-[2-nitro-4-(hydroxymethyl)phenyl]-2,3,4-tri-O-acetyl-β-D-glycopyranuronate in CH$_2$Cl$_2$ with methanesulfonyl chloride and triethylamine to give methyl 1-O-[4-(methanesulfonyloxymethyl)-2-nitrophenyl]-2,3,4-tri-O-acetyl-β-D-glycopyranuronate;
(f) reacting methyl 1-O-[4-(methanesulfonyloxymethyl)-2-nitrophenyl]-2,3,4-tri-O-acetyl-β-D-glycopyranuronate with a suspension of BQC and Cs$_2$CO$_2$ in anhydrous DMF and purified on silica gel to give 10-[4-O-(methyl-2,3,4-tri-O-acetyl-β-D-glycopyranuronate)-3-nitrobenzyloxy]5,6-dihydro-4H-benzo[de]quinoline-camptothecin;
(g) reacting a suspension of 10-[4-O-(methyl-2,3,4-tri-O-acetyl-β-D-glycopyranuronate)-3-nitrobenzyloxy]5,6-dihydro-4H-benzo[de]quinoline-camptothecin with sodium hydroxide in anhydrous MeOH to produce 10-[4-O-(methyl-β-D-glycopyranuronate)-3-nitrobenzyloxy]5,6-dihydro-4H-benzo[de]quinoline-camptothecin; and
(h) purifying 10-[4-O-(methyl-β-D-glycopyranuronate)-3-nitrobenzyloxy]5,6-dihydro-4H-benzo[de]quinoline-camptothecin to give 10-[4-O-(β-D-glucopyranuronate)-3-nitrobenzyloxy]camptothecin.

\* \* \* \* \*